United States Patent [19]

Giunta

[11] Patent Number: 4,731,082
[45] Date of Patent: Mar. 15, 1988

[54] PRE-MAXILLARY IMPLANT
[76] Inventor: Stephen X. Giunta, 4600 King St., Alexandria, Va. 22302
[21] Appl. No.: 77,121
[22] Filed: Jul. 21, 1987
[51] Int. Cl.$^4$ .............................................. A61F 2/18
[52] U.S. Cl. .................................................... 623/10
[58] Field of Search ................... 623/10, 16; D24/33; 128/342

[56] References Cited
U.S. PATENT DOCUMENTS

| D. 127,595 | 6/1941 | Vivian | D24/33 |
|---|---|---|---|
| D. 270,759 | 9/1983 | Straith | D24/33 |
| D. 290,878 | 7/1987 | Giampapa | 623/16 |
| 1,597,331 | 8/1926 | Thurston | 128/342 |

Primary Examiner—Richard J. Apley
Assistant Examiner—James Prizant

[57] ABSTRACT

A pre-maxillary implant device to be surgically inserted in the pre-maxillary area of the human face to increase the protrusion of the base of the nose, in the form of a unitary integral laterally elongated body of semi-solid plastic material including a central riser formation forming an upright pedestal portion for supporting the mesial crura having a convex front face extending upwardly along an arcuate path having an approximately 70° posterior inclination and having a concave rear face provided with a posterior notch to fit against the anterior nasal spine, the pedestal portion to be inserted under the DSN muscle to provide a foundation for nasal base protrusion and tip projection. The implant member has a substantially flat horizontal bottom surface across the entire width thereof and the pedestal portion has a substantially flat top surface of less lateral span than the bottom surface, and a pair of relatively thin opposite lateral extensions providing wing formations projecting from the lowermost portions of the pedestal portion and terminating in vertically enlarged terminal formations providing support for the lateral alar bases.

14 Claims, 7 Drawing Figures

PRE-MAXILLARY IMPLANT

BACKGROUND AND OBJECTS OF THE INVENTION

The present invention relates in general to a pre-maxillary implant, and more particularly to an implant device to be surgically inserted in the pre-maxillary area of the face to increase the protrusion of the base of the nose, adding support to this area by increasing the mask of the pre-maxilla.

One of the unfortunate consequence of primary rhinoplasty can be the formation of an excessively retruding or acute naso-labial angle due to columellar retraction. This in turn causes loss of, or failure to achieve proper tip projection. The real basis for this is lack of protrusion of the whole nasal base which consists of alae, base of nostrils and columella.

Since the nasal base rests on the pre-maxillary area, i.e., the upper base of the alveolar processes between the pyriform apertures and alveolar eminences, attention to this area is necessary for successful primary and secondary rhinoplastry. Augmenting this area is certainly nothing new. Over 25 years ago Aufricht described the use of cartilage grafts of silicone implants behind the upper lip together with a columnellar "orthopedic" suture which also narrows the nostrils. Guerro-Santos has recommended a similar procedure. Hindered has devised an implant inserted by extending the transfixion incision to section the Depressor-septi-nasi muscle. Carroni has proposed a transversely inserted step-like silicone implant with the highest step at the columella-labial angle.

The present invention is a novel pre-maxillary implant to be introduced in the sublabial area, designed to achieve improved protrusion of the nasal base and in turn producing proper tip projection. This implant configuration pays particular attention to increasing the protrusion of the boney foundation of the nasal base, i.e. the pre-maxillary area, to properly support the tip and very importantly the laterial alae. If this is not achieved, then the various techniques previously proposed for top projection, such as the Goldman tip, L-shaped implants, shield grafts, bunching sutures, etc. can achieve only limited success at best, and at worst fail to achieve desired results. It is essential that proper foundation from below be provided for the tip to be projected above.

The causes of improper tip projection fall, like everything else into two broad categories: heredity and environment. Within the scope of the latter are trauma, infection or iatrogenic causes such as excessive reaction of the candal end of the cartilegeous septum, improper management of the membranous septum, excessive resection of the alar cartilages or removal of the anterior nasal spine. Within the scope of heredity are a retracted lower base of the nose found more commonly in the non-caucasian. In some patients, the retroposition of the maxilla along with a posterior and inferior inclination or absence of the anterior nasal spine produce a prognathic facial appearance which if severe is called, most unattractively, an "ape lip" deformity. Since the growth of the maxilla is achieved by advancement and resorption of the bone in these directions, it is not difficult to see how these "deformities" result. In others, this appearance is due to a decreased dental-axial angle in relation to the anterior nasal spine. This angle, as described by Schule as between the upper central incisors and the anterior nasal spine plane to be considered aesthetically normal is 70° (seventy). This is combined with a retroposition of the upper alveolar process and sometimes with a short columella thus increasing the retrusion of the nasal tip. If the maxilla is severly retruded, a long flat lip with a gummy smile can result. Also this causes the melolabial fold to be closer to the alar groove and therefore more accentuated.

While wrestling with the problem of tip projection, after experiencing my share of failures both in primary and revision surgery, I became increasingly aware that the real problem was lack of protrusion of the entire base of the nose and support had to be added to this area by increasing the mass of the pre-maxilla. Many times enough cartilage was not present from grafting and small pieces of silicone did not work well since these were placed only at the feet of the mesial crura and accurate suturing was sometimes difficult. In some individuals, I was able to harvest an adequate cartilage graft from the the xiphoid process of the sternum. This has distinct advantages over costal or costochondral grafts.

I therefore consider that these problems can be alleviated by providing a specially designed and configuration implant, for example, of semi-solid silastic, having a central riser or upright pedestal portion for support of mesial crura with a groove to insert a strut, if needed, and a 70° posterior inclination. The pedestal portion is provided with a posterior notch to provide fit against the anterior nasal spine, and thinner lateral extensions project to either side for normal nostril contour. Posterior extensions are provided for support of lateral alar bases. This is inserted using the sub-labial approach under the DSN muscle to provide a foundation for nasal base protrusion and tip projection.

Other objects, advantages and capabilities of the present invention will become apparent from the following description, taken in conjunction with the accompanying figures illustrating a preferred embodiment of the invention.

DETAILED DESCRIPTION OF A PREFERRED EMBODIMENT

Figure 1:
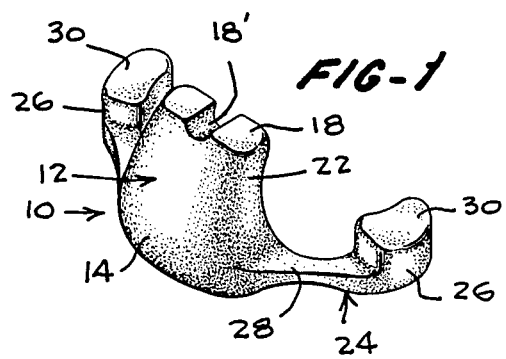
FIG. 1 is a front perspective view of the pre-maxillary implant of the present invention.
Figure 2:
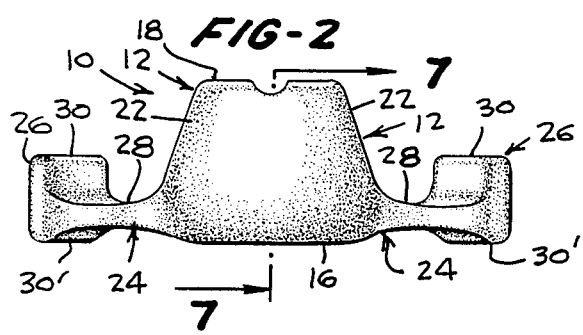
FIG. 2 is a front elevational view thereof.
Figure 4:
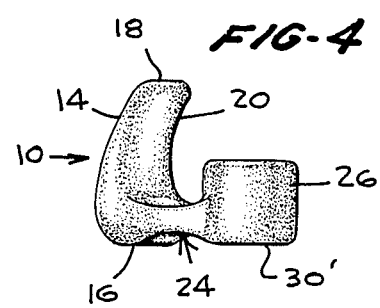
FIG. 4 is a side elevational view thereof from the right side of FIG. 2.
Figure 3:
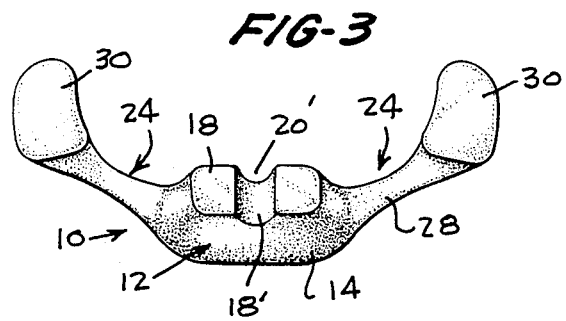
FIG. 3 is a top plan view thereof.
Figure 5:
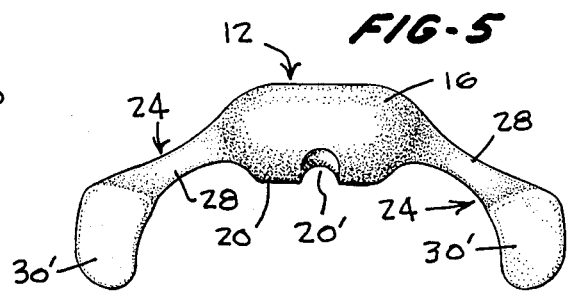
FIG. 5 is a bottom view thereof.
Figure 6:
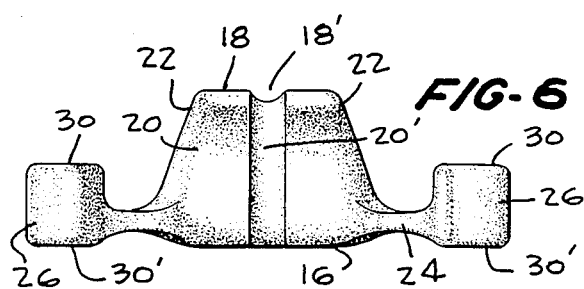
FIG. 6 is a rear elevational view thereof.
Figure 7:
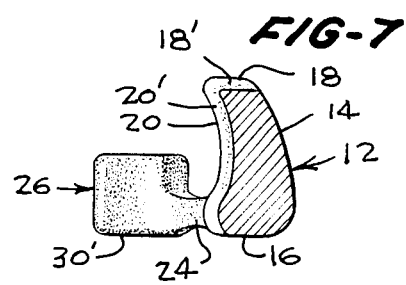
FIG. 7 is a vertical section view taken along the line 7—7 of FIG. 2.

Referring to the drawings, herein like reference characters designate corresponding parts throughout the several figures, there is shown a preferred form of my pre-maxillary implant, indicated generally by the reference 10, which is formed of a semi-solid silastic material shaped in a preferred manner to be inserted under the DSN muscle to provide a foundation for nasal base protrusion and tip projection. Specifically, the implant 10 comprises a central riser or upright pedestal portion 12, having an arched front surface 14 extending along an angle of about 70° posterior inclination from a horizontal flat base or bottom surface 16 to a flat upper or top surface 18 of less lateral span than the bottom surface portion 16. In front and rear profile, this central riser or upright pedestal portion 12 is of substantially isosceles trapezoidal or truncated triangular configuration, as will be most apparent from FIGS. 2 and 6, with slightly rounded edges at each of the junctures between the upper and lower surfaces 18 and 16 and the convexly curved front surface 14 and concavely curved rear surface 20. The rear surface 20 and the top surface 18 are interrupted by an upper notch 18' and a posterior notched 20', to provide fit against the anterior nasal spine. The central riser or pedestal portion 12 also has opposite vertically extending inclined side wall surfaces 22 extending in upwardly convergent relation and also having rounded junctures or corners with the front and back surfaces and the top and bottom surfaces of the pedestal portion.

Extending in opposite lateral directions from the lower most portion of the central riser or upright pedestal formation 12 are a pair of relatively thin opposite lateral extensions or wing formations 24 terminating in vertically enlarged tip or terminal formations 26 of the configuration shown. The intermediate arm portions 28 have flat horizontal upper and lower surfaces joining the central riser or upright pedestal formation 12 by rounded concave surfaces while the upper and lower surfaces 30, 30' of the terminal enlargements 26 of the lateral extensions are flat horizontal surfaces disposed parallel to each other and of generally foot shaped configuration in bottom and top plan view with the lower surface 30' lying substantially in the same plane as the flat horizontal lower most portion of the bottom surface 16.

The central riser or upright pedestal portion 12 forms support of the miesiel crucra and provides a groove to insert a strut if needed and includes along the front face 14 thereof the convex surface having a substantially 70° posterior inclination. The posterior notch 20' is provided to fit against the anterior nasal spine, as previously stated, and the implant includes the thinner lateral extensions 24 for normal nostril contour, the terminal formations 26 thereof providing posterior extensions for support of lateral alar bases.

To install the pre-maxillary 10, the sublabial area is infiltrated with the anesthetic-vasocontrictor of choice, with care being taken to prevent distortion. A midline vertical transfrenular incision is carried down to the periosteum. Using a small elevator, a small pocket is formed under the DSN muscle without severing it. Small lateral incisions in the muscle are sometimes needed to provide necessary room for the implant. The pocket extends from the anterior spine across the base of the pyriform aperture and then postero-laterally to the naso-alar groove on each side. Hemostasis is obtained using very light cautery and often times is not needed. The implant is folded upon itself inserted "feet first" and easily placed without sutures. A one layer closure using absorbable suture is done. No specific dressing other than tape is needed. Peri-operativie antibiotics are normally used for a selected post-operative period.

By this arrangement, using the sublabial approach, preservation of the intact depressor septi nasal (DSN) muscle is achieved, although occasionally it is rudimentary and severing is necessary. The indications for severing the DSN muscle are (1) removal of overprojecting anterior nasal spine, (2) lengthening a short columella, (3) lengthening the upper lip, and (4) hypermotile tip.

Advantages are realized by the sublabial approach as better visualization is achieved, preservation of continuity of mesial crura at columella-labial angle is realized, the DSN muscle is preserved with decreased pain, decreased swelling, decrease loss of sensation, and decreased loss of muscle function, resulting in natural look and feel. Better accuracy is achieved in placing the implant, and no suture of the implant is needed.

In one satisfactory example of the pre-maxillary implant for implantation in a male, the implant may have a width of about 40 mm between the outermost surfaces of the terminal formations 26 with the height of the terminal formations 26 being about 16 mm and their transverse width and fore-and-aft depth being about 6 mm and 10 mm. The width of the riser or pedestal formation 12 between the mid portions of the sides 22 and its height may be about 14 mm. Smaller implants for females should have proportionately smaller dimensions for these components. Obviously considerable variation may occur in the specific dimensions for the central pedestal and terminal formations, the length of the wings or lateral extensions, and the fore-and-aft and vertical dimensions of the implant portions to achieve proper protrusion of the nasal base and proper tip projection.

I claim:

1. A pre-maxillary implant device to be surgically inserted in the pre-maxillary area of the human face to increase the protrusion of the base of the nose, comprising a unitary integral implant member of semi-solid plastic material or the like, compatible upon insertion with surrounding tissue, comprising a laterally elongated body of a width providing opposite end portions of appropriate size to correspond substantially to the distance between the lateral alar bases of the recipient including a central riser formation forming an upright pedestal portion for supporting the miesiel crucra having a convex front face extending upwardly along an arcuate path having an approximately 70° posterior inclination and having a concave rear face, the pedestal portion being provided with a posterior notch extending substantially vertical along the mid-region of said rear face to provide fit against the anterior nasal spine, the pedestal portion to be inserted under the DSN muscle to provide a foundation for nasal base protrusion and tip projection, the implant member having a substantially flat horizontal bottom surface across the entire width thereof and the pedestal portion having a substantially flat top surface of less lateral span than the bottom surface, and a pair of relatively thin opposite lateral extensions providing wing formations projecting from the lowermost portions of the pedestal portion and terminating in vertically enlarged terminal formations providing support for the lateral alar bases.

2. A pre-maxillary implant as defined in claim 1, wherein said central riser formation is of substantially isosceles trapezoidal configuration in front and rear profile having slightly rounded edges at each of the junctures between the bottom and top surfaces and the convexly curved front face and the concavely curved rear face.

3. A pre-maxillary implant as defined in claim 1, wherein the substantially isosceles trapezoidal front profile configuration of the central riser formation provides upwardly convergent inclined side walls jointed by rounded junctures with said front and rear faces and with said top surface.

4. A pre-maxillary implant as defined in claim 2, wherein the substantially isosceles trapezoidal front profile configuration of the central riser formation provides upwardly convergent inclined side walls jointed by rounded junctures with said front and rear faces and with said top surface.

5. A pre-maxillary implant as defined in claim 1, wherein said terminal formations of said opposite lateral extension are vertically enlarged, generally foot shaped formations in top and bottom plan view with the lower surface thereof lying substantially in the same plane as the flat horizontal bottom surface of the central riser formation, and the extensions having intermediate arm portions having a vertical thickness less than half the vertical thickness of said terminal formations provided with substantially flat horizontal upper and lower surfaces rounded at their front and rear edges.

6. A pre-maxillary implant as defined in claim 2, wherein said terminal formations of said opposite lateral extension are vertically enlarged, generally foot shaped formations in top and bottom plan view with the lower surface thereof lying substantially in the same plane as the flat horizontal bottom surface of the central riser formation, and the extensions having intermediate arm portions having a vertical thickness less than half the vertical thickness of said terminal formations provided with substantially flat horizontal upper and lower surfaces rounded at their front and rear edges.

7. A pre-maxillary implant as defined in claim 3, wherein said terminal formations of said opposite lateral extension are vertically enlarged, generally foot shaped formations in top and bottom plan view with the lower surface thereof lying substantially in the same plane as the flat horizontal bottom surface of the central riser formation, and the extensions having intermediate arm portions having a vertical thickness less than half the vertical thickness of said terminal formations provided with substantially flat horizontal upper and lower surfaces rounded at their front and rear edges.

8. A pre-maxillary implant as defined in claim 4, wherein said terminal formations of said opposite lateral extension are vertically enlarged, generally foot shaped formations in top and bottom plane view with the lower surface thereof lying substantially in the same plane as the flat horizontal bottom surface of the central riser formation, and the extensions having intermediate arm portions having a vertical thickness less than half the vertical thickness of said terminal formations provided with substantially flat horizontal upper and lower surfaces rounded at their front and rear edges.

9. A pre-maxillary implant as defined in claim 1, wherein said implant device is a molded semi-solid silastic body.

10. A pre-maxillary implant as defined in claim 2, wherein said implant device is a molded semi-solid silastic body.

11. A pre-maxillary implant as defined in claim 3, wherein said implant device is a molded semi-solid silastic body.

12. A pre-maxillary implant as defined in claim 4, wherein said implant device is a molded semi-solid silastic body.

13. A pre-maxillary implant as defined in claim 5, wherein said implant device is a molded semi-solid silastic body.

14. A pre-maxillary implant as defined in claim 6, wherein said implant device is a molded semi-solid silastic body.

* * * * *